United States Patent [19]

Siddiqi

[11] 4,353,983

[45] Oct. 12, 1982

[54] ANALYTICAL PROCESS AND MEANS FOR MEASURING THE AMOUNT OF HYDROGEN PEROXIDE IN AQUEOUS MEDIA AND OF ORGANIC SUBSTRATES GENERATING HYDROGEN PEROXIDE BY ENZYMATIC OXIDATION

[75] Inventor: Iqbal Siddiqi, Geneva, Switzerland

[73] Assignee: Battelle Memorial Institute, Carouge, Switzerland

[21] Appl. No.: 205,325

[22] PCT Filed: Nov. 13, 1979

[86] PCT No.: PCT/EP79/00089

§ 371 Date: Jul. 15, 1980

§ 102(e) Date: Jul. 10, 1980

[87] PCT Pub. No.: WO80/01081

PCT Pub. Date: May 29, 1980

[30] Foreign Application Priority Data

Nov. 15, 1978 [CH] Switzerland .................. 11718/78

[51] Int. Cl.$^3$ .................. C12Q 1/60; C12Q 1/54; C12Q 1/28
[52] U.S. Cl. .................. 435/11; 435/14; 435/25; 435/28; 435/817; 23/230 B; 204/1 T; 204/195 B
[58] Field of Search .................. 435/11, 14, 25, 28, 435/817; 204/1 T, 195 B, 195 R, 195 M; 23/230 B, 230 R; 424/2

[56] References Cited

U.S. PATENT DOCUMENTS

| | | | |
|---|---|---|---|
| 3,483,112 | 12/1969 | Ross | 204/1 T |
| 3,595,755 | 7/1971 | Hürtel | 435/14 |
| 3,902,970 | 9/1975 | Levin | 204/1 T |
| 4,098,574 | 7/1978 | Dappen | 435/14 |

FOREIGN PATENT DOCUMENTS

| | | |
|---|---|---|
| 2331017 | 6/1977 | France . |
| 339755 | 9/1959 | Switzerland . |

OTHER PUBLICATIONS

Hughes, et al., "Studies in Peroxidase Action, Part IX, Reactions Involving the Rupture of C—F, C—Br, and C—I Links in Aromatic Amines", *J. Chem. Soc.*, (1954), pp. 4630–4634.

Saunders et al., *Peroxidase*, Buttersworths & Co., Washington, (1964), pp. 24, 25, 204, 205.

*Primary Examiner*—Thomas G. Wiseman
*Attorney, Agent, or Firm*—Karl F. Ross

[57] ABSTRACT

The present invention relates to the quantitative determination of hydrogen peroxide in water media and of substrates capable of being oxidized enzymatically with the formation of $H_2O_2$ as well as the enzymes which are involved in such reaction and also the peroxidase which catalyzes the oxidation by $H_2O_2$ of other substrates.

13 Claims, 12 Drawing Figures

ANALYTICAL PROCESS AND MEANS FOR MEASURING THE AMOUNT OF HYDROGEN PEROXIDE IN AQUEOUS MEDIA AND OF ORGANIC SUBSTRATES GENERATING HYDROGEN PEROXIDE BY ENZYMATIC OXIDATION

BACKGROUND OF THE INVENTION

The measurement of hydrogen peroxide concentration in aqueous systems is important in many cases such as, for instance, when using $H_2O_2$ as an oxidant for the treatment of effluents (see W. H. KIBBEL, Peroxide Treatment of Industrial Waste Waters, Industrial Water Engineering, August-September 1976) and in medical diagnostic analysis. Thus, in connection with the medical aspect, many analytical techniques exist based on enzymatic oxidation reactions which involve the quantitative production of $H_2O_2$. Such techniques are particularly valuable because of the highly selective and sensitive behavior of some enzymatic systems toward specific substrates.

Thus, it is well-known to use an "oxidase" for catalyzing the quantitative oxidation of a substrate with the formation of a corresponding amount of hydrogen peroxide. This $H_2O_2$ can be thereafter measured by another enzymatic reaction in which an indicator dye is oxidized by this $H_2O_2$ in the presence of a peroxidase whereby the intensity of the color developped is a measure of the amount of the $H_2O_2$ present in the system and, consequently, a measure of the amount of the substrate originally present which generated the said $H_2O_2$ upon oxidation.

The "oxidase" enzymes suitable for such determination are usually named from the type of substrate they can act upon; thus, glucose oxidase specifically catalyzes the oxygen oxidation of glucose into gluconic acid with liberation of $H_2O_2$; cholesterol oxidase acts similarly toward cholesterol, etc.

DESCRIPTION OF THE PRIOR ART

Examples of oxidases can be found in the literature familiar to those skilled in the art, namely in "Enzyme Nomenclature Recommendations" (1972), International Union of Biochemistry, Elsevier Scientific Publishing Co.

There exists also several different peroxidases which are suitable for catalyzing such oxidations by $H_2O_2$ among which the peroxidases of horse-radish and of Japanese-radish are well-known. Various peroxidases are described by BOYER et al. in "The Enzymes" Vol. 8 (1963), Academic Press. Moreover, hemoglobin, or rather some of its constituents, can also act as a peroxidase in some cases.

Besides the method mentioned heretofore, several other enzymatic routes can be used for determining substrates in biological fluids, for instance glucose in blood or urine. Thus, besides titrating the $H_2O_2$ formed by the glucose oxidase catalyzed oxidation reaction by quantitatively oxidizing a dye in the presence of peroxidase, the amount of said $H_2O_2$ can also be measured polarographically by means of an electrode equipped with a semi-permeable membrane. Otherwise, instead of measuring the $H_2O_2$ formed, the oxygen consumed in the oxidation of glucose can also be measured with an electrode provided with a gas permeable membrane, e.g. an electrode such as the well-known "CLARK" electrode.

However, the above analytical procedures are not free from some drawbacks. For instance, the colorimetric method requires that the sample be inherently colorless and not turbid, otherwise significant measurement errors may result. Also, in connection with the electrometric methods involving membranes, the latter will require to be maintained carefully, otherwise bacterial contamination may occur with eventual spoiling of the electrodes. It is also desirable to have a general system and method enabling to determine either organic substrates that will generate $H_2O_2$ upon enzymatic oxidation, or the $H_2O_2$ formed during this oxidation, or even the enzymes themselves that act as catalysts in such reactions.

OBJECT OF THE INVENTION

The present invention proposes to remedy the above drawbacks and provide a versatile analytical method and apparatus.

SUMMARY OF THE INVENTION

The present invention utilizes the known phenomenon that some fluoro-compounds are oxidized by $H_2O_2$ in the presence of peroxidase with the quantitive splitting of the fluorine atom into fluoride ion. This is described in "Inorganic Biochemistry", Vol. 2, chapter 28, pages 1000–1001, (1964) Elsevier Scientific Publ. Co. in connection with some investigations on the peroxidase oxidation of organic halogen compounds having stable C—F, C—Br and C—I bonds.

One compound which is particularly suitable in connection with this reaction is p-fluoroaniline.

I have discovered that the $F^-$ ions generated during this reaction can be easily and precisely measured with an $F^-$ selective electrode, for instance of the following type: "96-09" made by ORION RESEARCH Inc., Cambridge, Mass., USA.

Hence, the method of the invention quantitatively determines, in aqueous media, either one of the two following constituents: $H_2O_2$ or peroxidase, comprises reacting this medium with an excess of an organic fluoro-compound the C—F bond of which is splittable by the peroxidase catalyzed action of $H_2O_2$ with resulting liberation of fluoride anion, and electrochemically measuring the rate of formation of the latter by means of a fluoride selectively sensitive electrode.

Since Or, in other words, the rate of $F^-$ production is proportional to the amount of $H_2O_2$, the concentration of peroxidase can be kept constant; alternatively, this rate is proportional to the amount of peroxidase present if the amount of $H_2O_2$ present is large enough for allowing the quantity consumed during the measurement reaction to be neglected. Therefore, the conditions of analysis must be adapted for either one or the other type of measurement.

The $F^-$ concentration with time is measured electrometrically with an electrode which is very sensitive to $F^-$ ions but very insensitive to the other substances present in the sample. This is one of the advantages of the method. Another advantage is that such electrode is inherently sturdy, relatively insensitive to shock and easy to maintain and to calibrate which makes it significantly more easy to operate than the electrodes of the prior art.

The method of the invention is based on the electrochemical measurement of $F^-$ ion produced by the reaction:

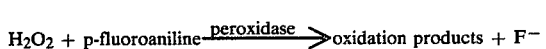
$$H_2O_2 + \text{p-fluoroaniline} \xrightarrow{\text{peroxidase}} \text{oxidation products} + F^- \quad (1)$$

Naturally, the same basic technique can be applied to the case when the hydrogen peroxide is formed in situ by some enzymatic oxidation of a substrate. Thus, in the case glucose is oxidized in the presence of glucose oxidase with simultaneous formation of $H_2O_2$, the latter or the glucose oxidase used can be measured by the above method. Consequently, the present invention also deals with the measuring of glucose and, alternatively, oxidase according to the following set of reactions:

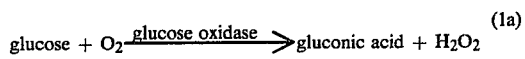
$$\text{glucose} + O_2 \xrightarrow{\text{glucose oxidase}} \text{gluconic acid} + H_2O_2 \quad (1a)$$

and reaction (1) just mentioned above.

Similarly, the method of the invention also applies to the determination of other substrates the catalytic oxidation of which involves the quantitative formation of hydrogen peroxide. This is for example the case of cholesterol which oxidizes in the presence of cholesterol oxidase.

The general principle of the method and its applications can be explained briefly as follows: The basic system of the invention consists in having present together, in a buffer, suitable quantities of $H_2O_2$, a peroxidase and the fluoro-compound. $H_2O_2$ is the oxidant and the peroxidase acts as the catalyst in the oxidation of the p-fluoroaniline which behaves as the acceptor and is used in relatively large excess for avoiding its actual consumption to influence the rate equation. Therefore, the reaction rate will be related to the respective concentrations of $H_2O_2$ and peroxidase. If peroxidase (the catalyst) is kept constant for a given set of measurements the reaction will be related to the amount of $H_2O_2$ and various quantities of the latter can be measured by measuring the corresponding rate of $F^-$ formation resulting from the p-fluoroaniline oxidation. Further, if rate measurements are taken over a very short period during which the change in concentration of the $H_2O_2$ can be neglected, the reaction becomes pseudo-zero order which facilitates computing the rate results. When it is wished to measure peroxidase instead of $H_2O_2$ with the present system, allowance is made for having a large excess of $H_2O_2$ relative to peroxidase (saturating $H_2O_2$), whereby the consumption of said hydrogen peroxide can be practically neglected and the measured rate of $F^-$ formation is proportional to the amount of peroxidase.

When the above system is to be used for the determination of precursor systems involving the oxidation of an organic substrate in the presence of the corresponding oxidase and formation of $H_2O_2$, the approach is similar to what is explained above. Thus, if the system involved concerns, for instance, the oxidation of glucose by oxygen in the presence of glucose oxidase and it is wished to measure the glucose contained in a sample, the conditions will be adapted for having the $H_2O_2$ produced by the oxidation of glucose be consumed by the peroxidase catalyzed reaction at a rate much faster than that of the formation of said $H_2O_2$ itself. Hence, the liberation rate of $F^-$ will then be a measure of $H_2O_2$ formation in the oxidation of glucose. Such conditions can be achieved because the peroxidase reaction is, per se, much faster than the oxidase reaction and because the relative amount of the respective enzymes in the system can be adapted, from case to case, to maintain such conditions valid by the usual means familiar to people skilled in the art.

Thus, in the presently exemplified situation, either the glucose can be determined in the presence of a suitable and fixed amount of oxidase, or the oxidase itself can be determined in the presence of a "saturating" quantity of glucose. The general scheme is adaptable, from case to case, to other systems involving organic substrates and corresponding oxidases.

Naturally, other electrodes than the type mentioned earlier are also suitable for being used in the method of the invention provided they are specifically adapted for the determination of $F^-$ ions in the presence of other dissolved substances. When these conditions are met, the electrode can be combined with a reference electrode of a classical type and the electrode system can be connected to any suitable reading device for recording the measured electrochemical parameters (amplifier, meter, recorder, etc.), as will be seen hereinafter in greater detail.

From a practical standpoint the general analytical scheme, illustrated for example in the case where $H_2O_2$ is measured, is as follows: The sample to be measured (solution of $H_2O_2$ is mixed with a reagent solution containing the peroxidase and an excess of p-fluoroaniline and the rate of $F^-$ liberation is measured at constant temperature (room or any other suitable controlled temperature) with the electrode system. If the analytical sample does not already contain the $H_2O_2$ to be measured, i.e. if the analysis concerns the measuring of a substrate generating the $H_2O_2$ upon enzymatic oxidation, (for instance glucose) the reagent solution will also contain the corresponding oxidase. If it is desired to measure glucose-oxidase instead of glucose, then the system will contain an excess of glucose. As mentioned earlier, in this case the generation of $H_2O_2$ is the rate determining step and the actual observed rate of $F^-$ liberation will then correspond to the rate of oxidase catalyzed oxidation of glucose.

In order to determine the rate of $F^-$ liberation for an unknown sample, reference may be had to a calibration curve. A calibration curve can be obtained by measuring, as described above, a series of samples containing known concentrations of $H_2O_2$. For each sample the rate of $F^-$ is recorded and the slope of the rate curves, at a time (which is of course the same for each sample) where the rate curves are about straight, is measured. Then, these slopes are plotted against $H_2O_2$ concentration thus providing the standard reference curve. The measured electrometric parameters to be used in determining the rate curves can be the voltage readings of the electrode system (mV) or, better, the corresponding $[F^-]$ values as calculated from the Nernst equation which, in this case, has the form of:

$$E = E' - S \cdot \log[F^-]$$

where E is the recorded potential and $E'$ is a constant inherent to the system which is determined experimentally and which involves the activity factors and the liquid junction potentials. S is the "Nernst slope" which is also constant and is to approximately 59 mV for a change of 10 units in the concentration of $F^-$ where the latter is expressed in moles/l. If the [F$^-$] values calculated from the above relation are used in the rate curves instead of the mV values, straighter rate curves are obtained, the slope of which is easier to determine and which permit drawing more accurate reference graphs.

Thus, the present analytical process and system which makes use of any type of existing F$^-$ selectively sensitive electrode and any type of organic fluoro-compound susceptible of quantitatively generating F$^-$ ions by the catalytic oxidation thereof with H$_2$O$_2$, but preferably of p-fluoroaniline which is enzymatically oxidized by H$_2$O$_2$ in the presence of a peroxidase, enables the quantitative determination of a variety of chemical or biochemical constituents usually present in biological fluids such as blood, urine and saliva and which can be enzymatically oxidized (by air or O$_2$) with the formation of H$_2$O$_2$.

BRIEF DESCRIPTION OF THE DRAWINGS

The following examples will better illustrate the practical aspects of the invention with reference to the annexed drawings in which:

FIG. 6a is a plot of [F$^-$] versus time for the reaction involving the measuring of glucose oxidase in the presence of an excess of glucose and.

SPECIFIC DESCRIPTION AND EXAMPLES

Example 1

The following solutions were prepared:

(i) Enzyme solution S$_E$: 10 mg of horse-radish peroxidase (600 U) were dissolved in 10 ml of acetate buffer 0.05 M, pH 6.4.

(ii) Solution of organic fluoro-compound S$_{CF}$: 1.7 ml of glacial acetic acid and 1.74 g of NaCl were dissolved in 20 ml of H$_2$O to which were thereafter added enough water and 5 M NaOH solution to give 30 ml of acetate buffer at pH 5–5.5. Then, there were added 0.3 g of TWEEN 20 (polyethylene-oxide sorbitan monolaurate, ICI) and 0.2 g of sodium lauryl sulfate at a temperature of 60° C.; then, there was added a solution of 0.3 g of p-fluoroaniline in 20 ml H$_2$O and the mixture was stirred at 60° C. until a homogeneous solution was obtained. Then the solution was allowed to cool after which it was made up to 100 ml by adding some more water.

(iii) Reagent solution S$_R$: This was prepared just before use and involved the mixing of 5 ml of the solution S$_{CF}$ and 0.1 ml of the solution S$_E$.

Figure 1A:
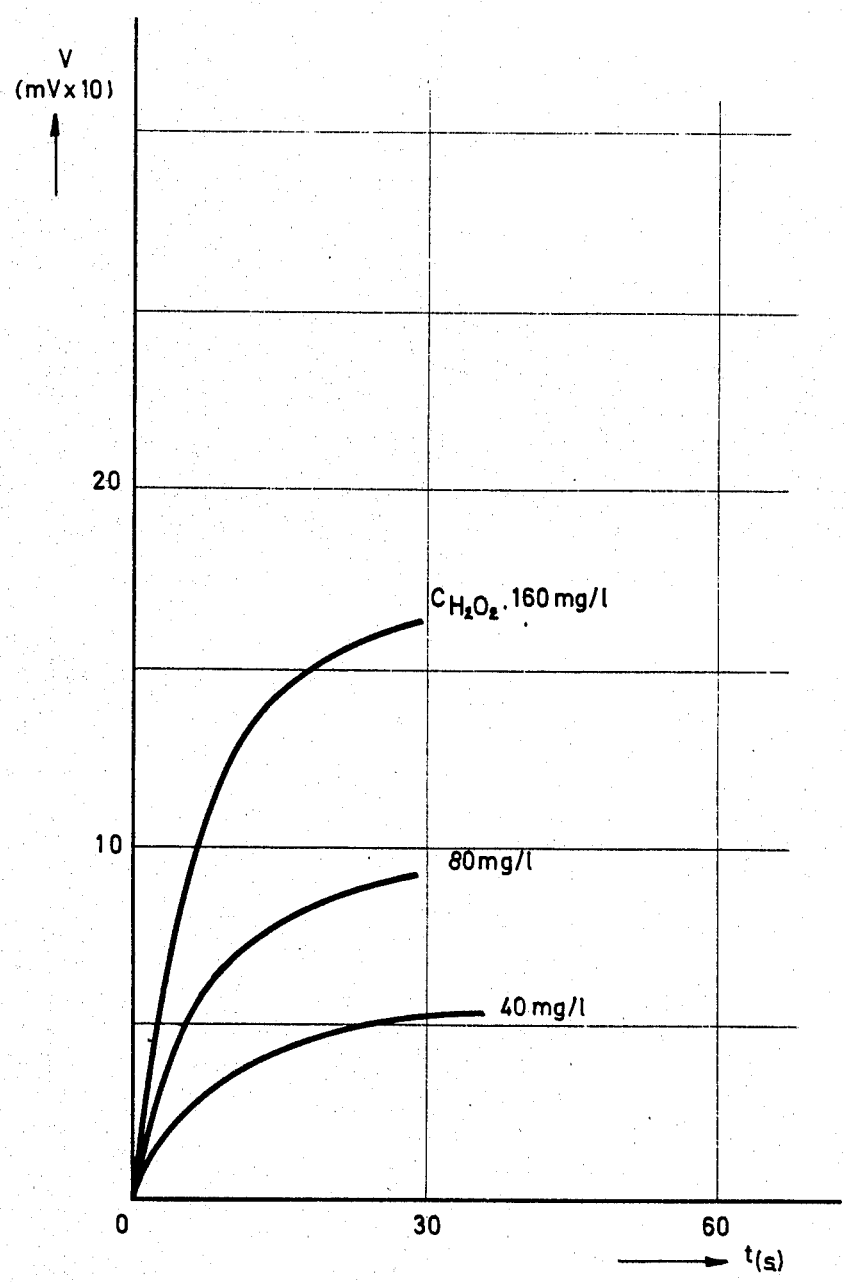
FIG. 1a illustrates the experimental calibration curves taken from Example 1 which show the potential (mV) variation of the electrode plotted against time for samples of different H$_2$O$_2$ concentrations.
Figure 1B:
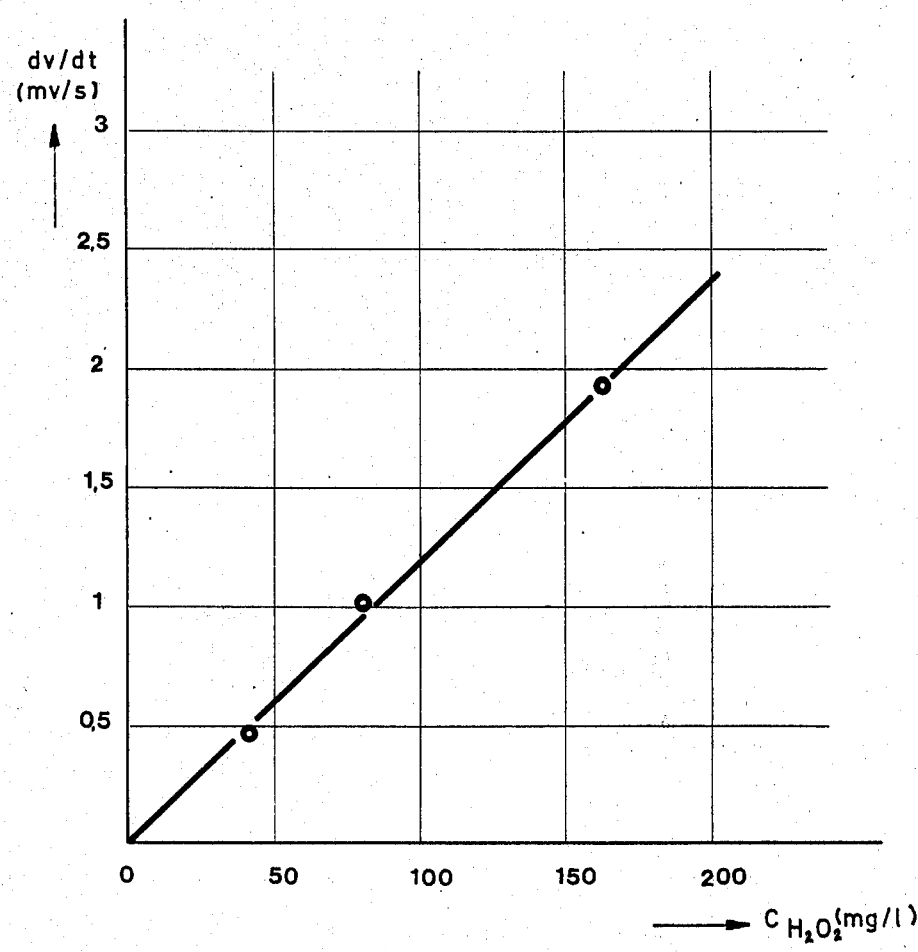
FIG. 1b is a graph obtained by plotting the initial slopes dV/dt of the rate curves of FIG. 1a versus the corresponding H$_2$O$_2$ concentrations.

Thus, 5.1 ml of the S$_R$ solution were placed in a plastic beaker and a F$^-$ selective electrode (Type 96-09, ORION RESEARCH) was introduced. This electrode had a reference electrode combined therewith but any other F$^-$ selective electrode with separate complementary electrode can also be used in the circuit. The electrode was connected to a suitable potentiometer, i.e. to a recording voltmeter of type "CORNING EEL 112 Digital Research pH meter" from CORNING SCIENTIFIC INST., Medfield, Mass. USA. The readings were in mV (relative). When the reading was stable, 0.1 ml of a calibrating solution of H$_2$O$_2$ was added under magnetic stirring. The calibrating H$_2$O$_2$ solution was any one of 0.4, 0.8 and 1.6 g/l H$_2$O$_2$ aqueous solutions. Then, the voltage readings began to change and were recorded automatically with time on the recording chart of the voltmeter. FIG. 1a shows the three curves which were recorded for the above three samples of H$_2$O$_2$. It can be seen that the initial part of each curve is reasonably straight. The slope of these curves was then plotted against corresponding H$_2$O$_2$ concentration which provided the graph of FIG. 1b. It can be noted that the curvatures of the rate curves of FIG. 1a are normal rate curvatures although a certain slowing-down of the reaction rate occurs with time due to some extent of poisoning of the enzymatic oxidation by the F$^-$ anions. The standard curve dV/dt of FIG. 1b is sufficiently straight for being used as a reference in the determination of unknown samples of H$_2$O$_2$. For such determination the unknown sample is treated exactly as described above, the kinetic curve is recorded, the slope at the proper point is measured and the corresponding concentration of the sample is determined by using the standard curve of FIG. 1b. Naturally, the standard curve can be extended to values below 0.4 g/l or beyond 1.6 g/l of H$_2$O$_2$ by using other calibrating samples of the desired concentrations.

Example 2

This Example concerns the analysis of glucose in aqueous solutions (see reactions (1a) and (1)):

(i) Enzyme solution $S_E$: Such a solution was prepared by dissolving 3000 U of glucose oxidase and 600 U of horse-radish peroxidase in 7 ml of 0.05 M acetate buffer (pH 6.4) and making it to 10 ml exactly with more buffer. The solution was stored at 3° C. before use.

(ii) Solution of p-fluoroaniline $S_{CF}$: This was identical with the corresponding solution of Example 1 with the only difference that 0.12 g of EDTA (ethylenediamine tetraacetic acid) were further added to complex metal ions possibly present in the samples and which might block some $F^-$ ions and vitiate the measurements.

Figure 2A:
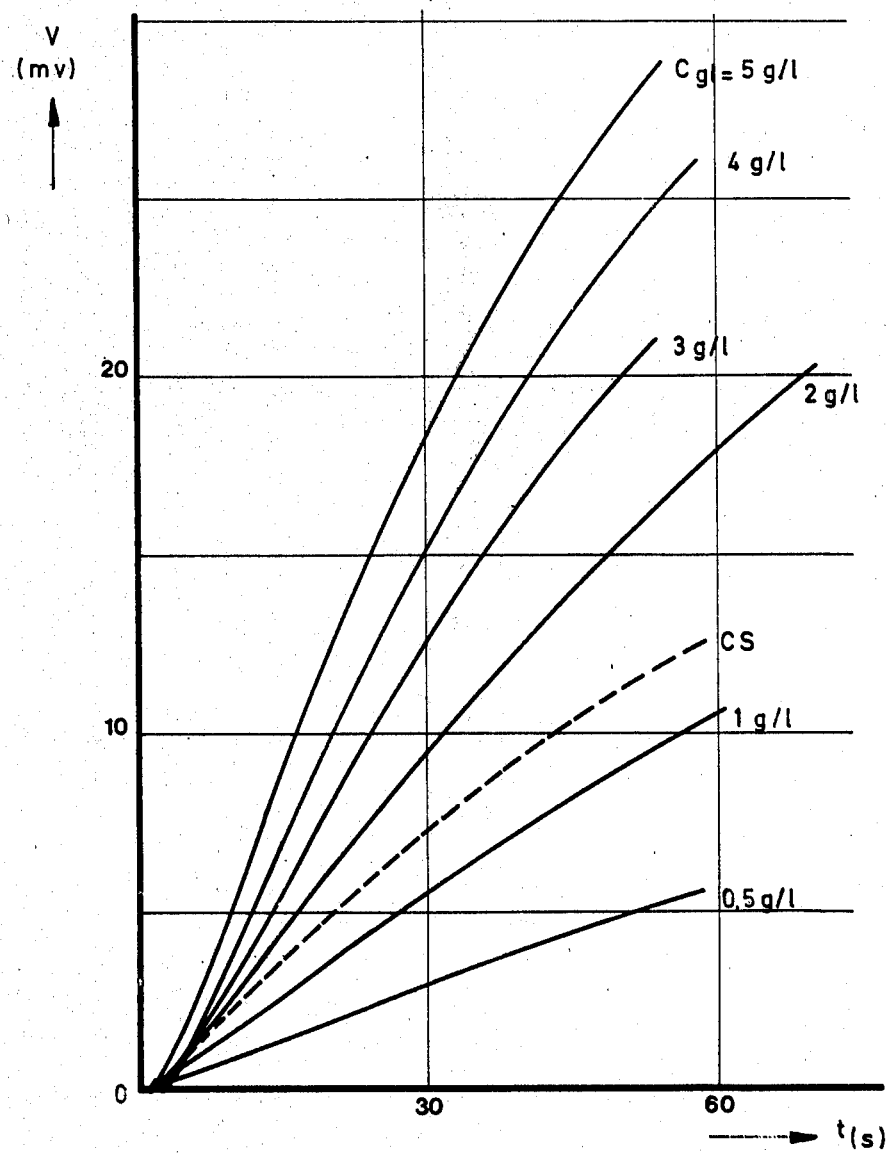
FIG. 2a is taken from the results of Example 2 and shows, as in FIG. 1a, the F$^-$ formation rate curves (mV versus time) measured in the case of the glucose oxidase oxidation of different samples of glucose solutions.

Then the preparation of a reference graph was performed as described in Example 1. 5 ml of solution $S_{C-F}$ and 0.1 ml of solution $S_E$ were placed in a polythene beaker to which were added, under agitation, 0.1 ml of a standard solution of glucose. Such standards were water solutions containing 0.5, 1, 2, 3, 4 and 5 g/l of glucose dissolved in a 1 g/l benzoic acid solution. The benzoic acid was used as a preservative. Then the rate curves were run and the recorded values reported on FIG. 2a, after which the slopes, determined on the straightest part of the curves, were used to make the standard graph of FIG. 2b.

Figure 2B:
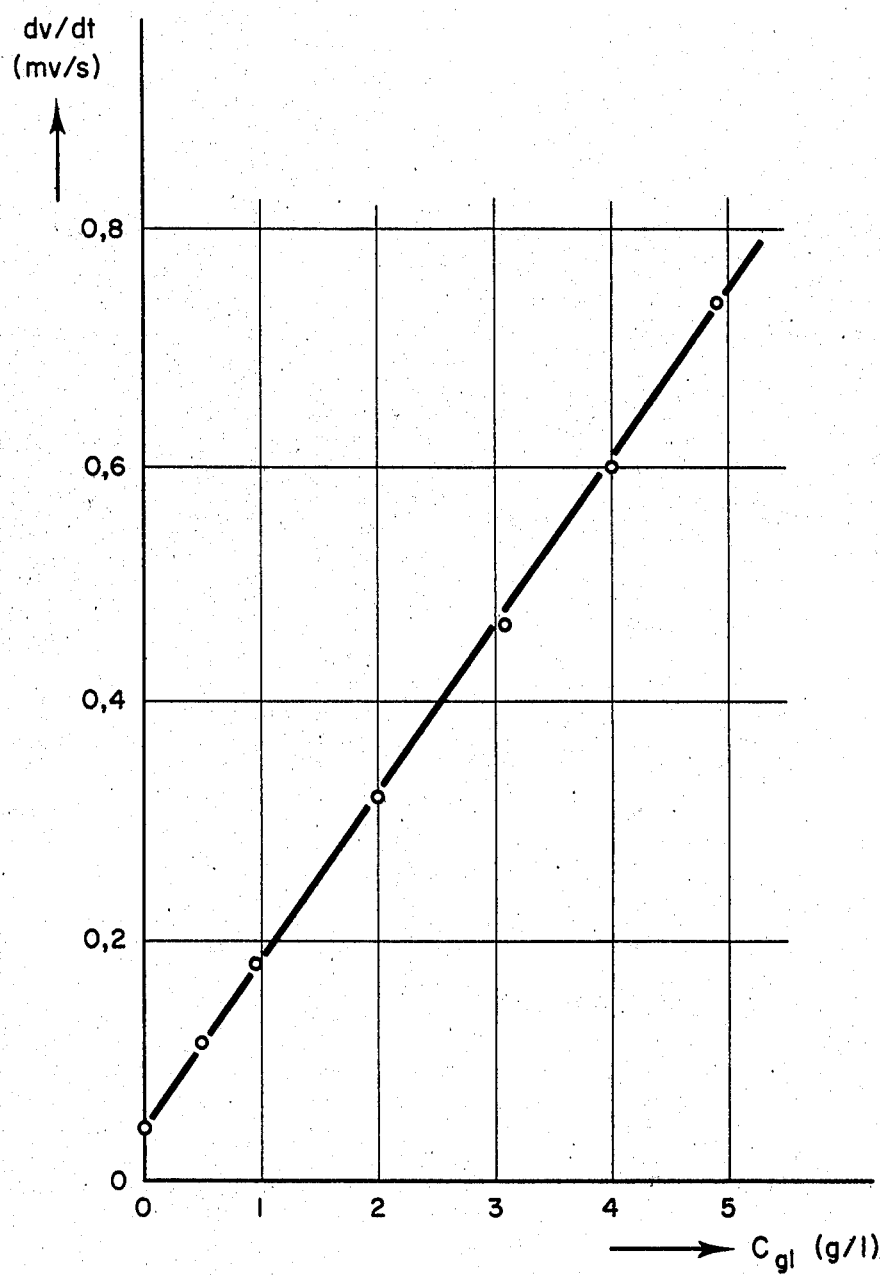
FIG. 2b shows as in FIG. 1b the plot of the slope d(mV)/dt of the curves of FIG. 2a versus the corresponding concentrations in glucose of the samples.

The standard curve of FIG. 2b was then used to determine the glucose concentration of an unknown sample by mixing 0.1 ml of said sample with 5 ml of the $S_{CF}$ solution and 0.1 ml of the $S_E$ solution and running the rate curve exactly as described above. The sample was a commercial control serum sample (Type P, Lot X-2739) from HOFFMANN-LA ROCHE & CO., Basel, Switzerland. This material was bought in lyophilized form and was diluted as directed by the data sheet. The results of the test are illustrated by curve CS on FIG. 2a. The slope of this curve was 0.348 mV/sec and corresponded to 2.18 g/l of glucose according to the chart of FIG. 2b. According to the manufacturer of the sample, other methods of the prior art for glucose determination had given the following analytical values:

| Analytical method | glucose concentration (g/l) | |
|---|---|---|
| | Average | Accepted interval |
| glucose oxidase + peroxidase + dianisidine (no deproteination) | 2.31 | 2.15–2.47 |
| Beckmann glucose analyzer | 2.27 | 2.11–2.43 |

Thus, the value measured by the means of the present invention fits well within the above-mentioned interval.

Figure 4A:
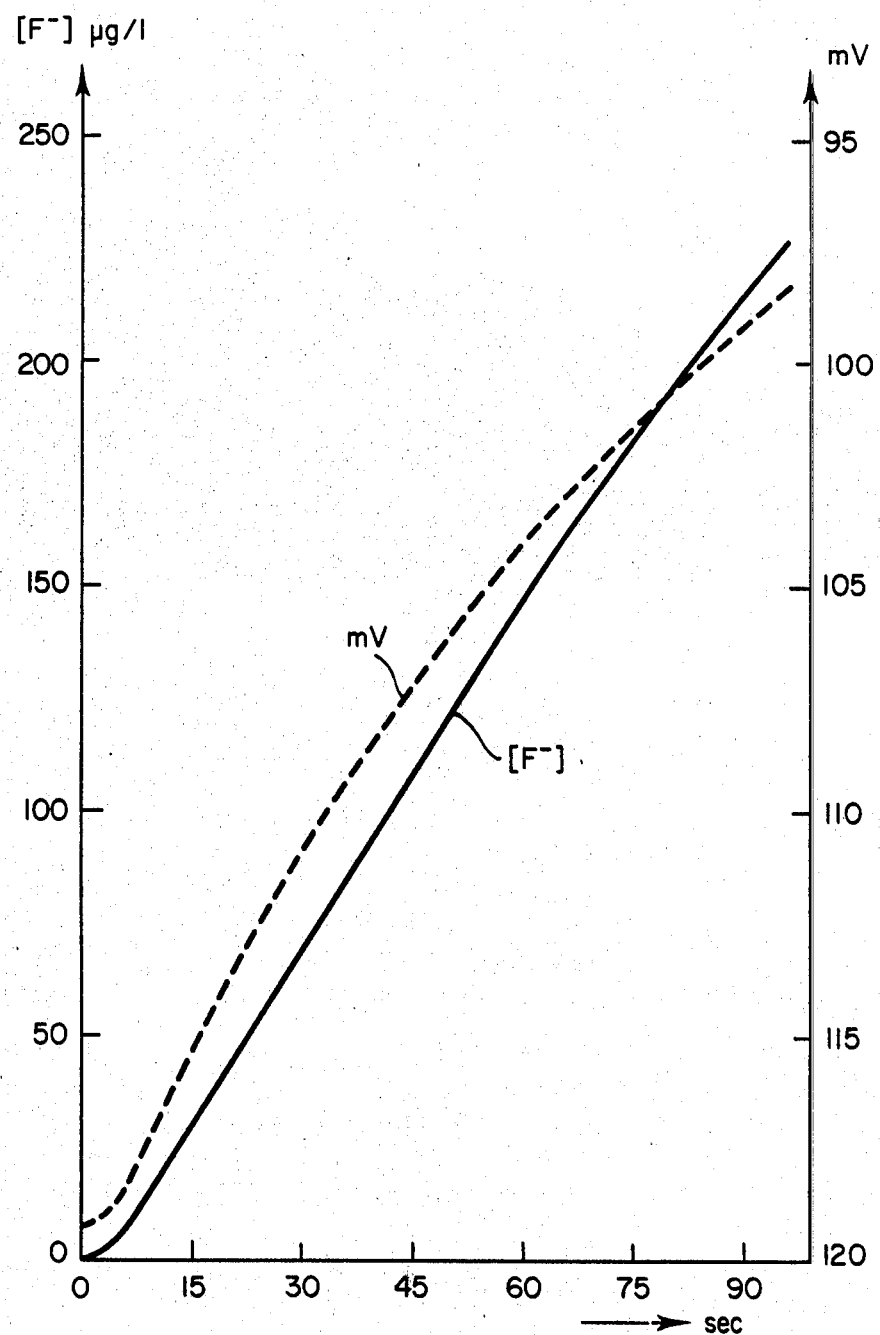
FIG. 4a is a graph similar to that of FIG. 2a but which shows, besides the interrupted line representing the time versus millivolt curve in the case of the analysis of a 2 g/l glucose solution whereby the catalyzed oxidation thereof provides the H$_2$O$_2$ necessary to the liberation of a corresponding amount of F$^-$, a rate curve (solid line) in which the concentration [F$^-$] in µg/l of the fluoride anion, calculated as shown above from the Nernst equation, is plotted versus time.

It should however be noted that, in order to improve the accuracy of the standard curve and, consequently, of the measurements, it may be advantageous to utilize, instead of the mV values directly furnished by the voltmeter, the corresponding $[F^-]$ values as calculated from the Nernst equation mentioned above. If a graph is prepared by plotting the calculated concentrations $[F^-]$ versus reaction time t (see FIG. 4a) a line is obtained, the slope of which is practically constant over a long period (about 6 to 100 sec); this is so because the curvature due to the existence of a log type correlation in the rate curve has been eliminated. It is therefore easier now with the curve of FIG. 4a to determine accurately the parameters governing the kinetics of the $F^-$ production than with the voltage rate curves of FIG. 1a or 1b. In general, it is advantageous to measure said slope at the time t=30 sec, zero time being at the moment when the electrode system has reached equilibrium. In this connection, it is also useful to mention that the addition of a small quantity of fluoride to the reaction mixture ($[F^-] \cong 10^{-5}$ M) is beneficial since it reduces the equilibration period to about 60 sec as compared to about 6 min without the additional fluoride. These improvements are further commented upon hereinbelow in connection with Example 4 and FIG. 4b in which the slopes measured as per FIG. 4a are plotted against the corresponding calibrating sample concentration.

Example 3

This Example deals with the analysis of cholesterol according to the reactions:

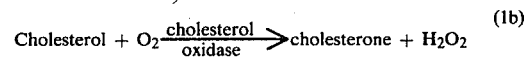

$$\text{Cholesterol} + O_2 \xrightarrow{\text{cholesterol oxidase}} \text{cholesterone} + H_2O_2 \quad (1b)$$

and the reaction (1) discussed above.

(i) Enzyme solution $S_E$: This solution was prepared by dissolving in 5 ml of 0.1 M phosphate buffer at pH 6.0, 100 U of cholesterol oxidase, 600 U of horse-radish peroxidase, 5 mg of TRITON X-100 (isooctyl-phenoxypolyethyleneglycol, ROHM & HAAS, USA). Then, further phosphate buffer was added to make 10 ml. The solution was stored between 1° and 5° C. before use.

(ii) Solution of p-fluoroaniline $S_{CF}$: This was prepared as in the previous Examples by dissolving at 60° C. in about 50 ml of 0.1 M phosphate buffer 0.3 g of TRITON X-100, 0,1 g of sodium cholate, 0.58 g of NaCl, then 0.3 g of p-fluoroaniline under stirring. When the solution was well homogeneous, it was allowed to cool and was completed to 100 ml with phosphate buffer.

(iii) Cholesterol standard samples $S_{CH}$: These were made by dissolving cholesterol (quality "PRECISET" from BOEHRINGER, Mannheim, Germany) in water, thus making samples at 1, 2, 3 and 4 g/l. Analyses were carried out on aliquots of 0.01 ml.

Figure 3A:
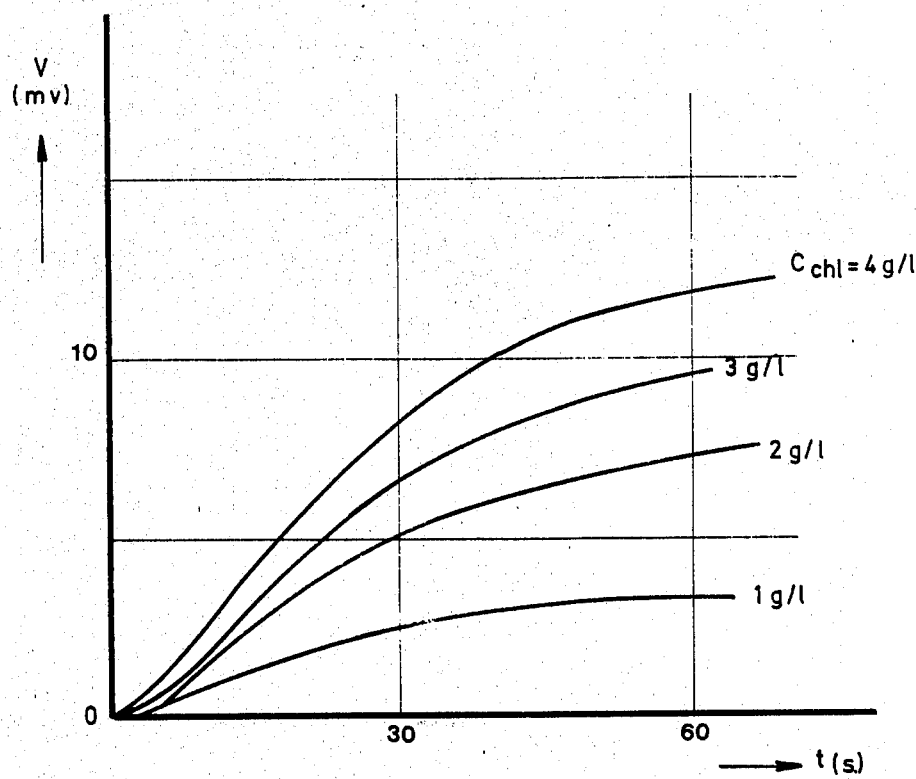
FIG. 3a illustrates experimental rate curves (mV versus time) similar to those of FIG. 2a but concerning the oxidation of cholesterol in the presence of cholesterol oxidase with formation of H$_2$O$_2$ and the corresponding liberation of F$^-$ ions by the quantitative oxidation of p-fluoroaniline with said H$_2$O$_2$.
Figure 3B:
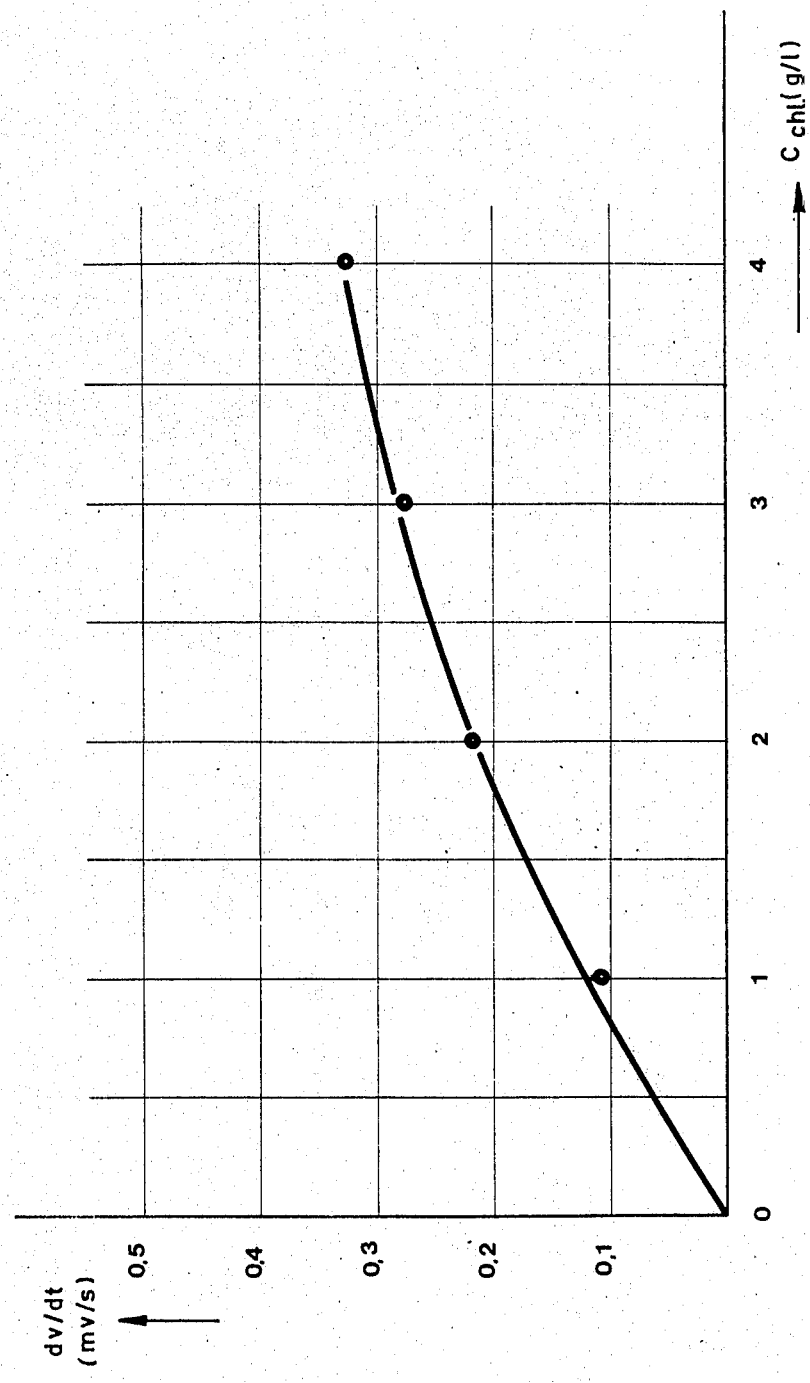
FIG. 3b is a standard curve obtained by plotting the dV/dt values of the curves of FIG. 3a against the cholesterol concentrations of the corresponding samples.

For the analysis itself, the same procedure described in the previous Examples was used: 5 ml of solution $S_{CF}$ and 0.1 ml of solution $S_E$ were agitated in a plastic beaker while measuring the potential by means of the $F^-$ sensitive electrode system described above. When equilibrium was reached, 0.01 ml of one of the samples $S_{CH}$ was added and the voltage change with time was recorded. The curves obtained are shown on FIG. 3a. Then the slopes of the curves were measured as in the previous Examples and the slope values plotted against the corresponding cholesterol concentration of the samples. This is shown on the graph of FIG. 3b which was thereafter used for determining the cholesterol in unknown solutions, aliquots of such solutions to be analyzed having been subjected to the same operational procedure than for the calibrating samples described above.

Example 4

This Example is particularly intended for illustrating the preparation of a standard graph by plotting the $d[F^-]/dt$ values versus the concentrations of the samples under analysis.

(i) Enzyme solution $S_E$: A 0.05 M acetate buffer was prepared according to usual procedures and a solution was prepared by dissolving 600 U of horse-radish peroxidase and 300 U of glucose oxidase in 10 ml of the buffer (pH=6.4). The $S_E$ solution was stored at 3° C. before use.

(ii) Solution of p-fluoroaniline $S_F$: This solution was made by dissolving in 199 ml of 0.5 ml acetate buffer, pH 5.5, 0.18 g of EDTA, 0.1 g of p-fluoroaniline and 1 ml of a $10^{-3}$ M solution of NaF.

Then, the analysis was carried out as in the previous Examples, working with 4.8 ml of solution $S_F$, 0.1 ml of solution $S_E$ and 0.1 ml of glucose solutions (see Table below) and operating under magnetic stirring in a polyethylene beaker. The voltage versus time curves were recorded and the mV readings at t=30 sec after equilibrium were converted to the corresponding [F$^-$] values by the above-discussed Nernst equation (μg/l units). The results are collected in the following Table.

TABLE

| Glucose concentration of the sample (g/l) | Voltage at 30 sec (mV) | [F$^-$] at 30 sec (μg/l) |
|---|---|---|
| 0.5 | 1.7 | 20 |
| 1 | 3.3 | 41 |
| 2 | 6.8 | 82 |
| 3 | 10.2 | 120 |
| 4 | 13.2 | 160 |
| 5 | 16.1 | 198 |
| 7.5 | 22.5 | 300 |
| 10 | 27.8 | 402 |

Figure 4B:
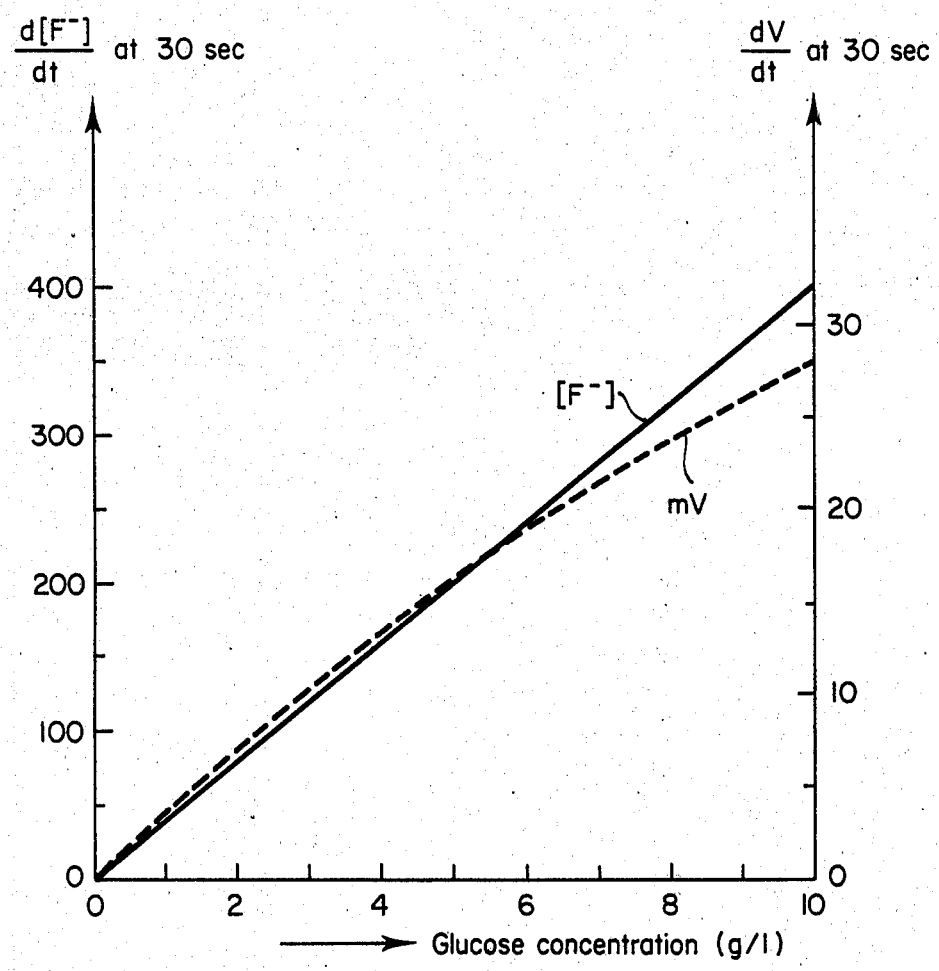
FIG. 4b is a graph showing the change; versus glucose concentration (as measured from a series of known samples), of the slope d(mV)/dt (interrupted line curve) and of the slope of the corresponding calculated values d[F$^-$]/dt.

These figures were used to prepare the graph of FIG. 4b. The dotted line on this graph represents dV/dt plotted versus glucose concentration whereas the full line represents d[F$^-$]/dt versus glucose concentration. The drawing clearly shows that the full line is straight within measurement errors. It was used as a standard for the evaluation of unknown glucose concentrations according to the procedure of the invention.

EXAMPLE 5

This Example reports the measuring of peroxidase in the presence of an excess of hydrogen peroxide.

(i) Solution of p-fluoroaniline $S_{CF}$: This solution was prepared as described in the previous Examples and consisted in a 100 ml solution of 0.3 M acetate buffer containing 0.5 g of p-fluoroaniline and 1 μmole of NaF ($10^{-5}$ M F$^-$ solution).

(ii) Hydrogen peroxide stock: This was a $10^{-2}$ M solution that is, containing 0.34 g of pure $H_2O_2$ in 1 liter of solution.

(iii) Peroxidase standard solution $S_E$: Such solutions were prepared which contained, respectively, 1.2, 2.4, 3.6, 4.8 and 6.0 U of enzymes per ml.

Figure 5A:
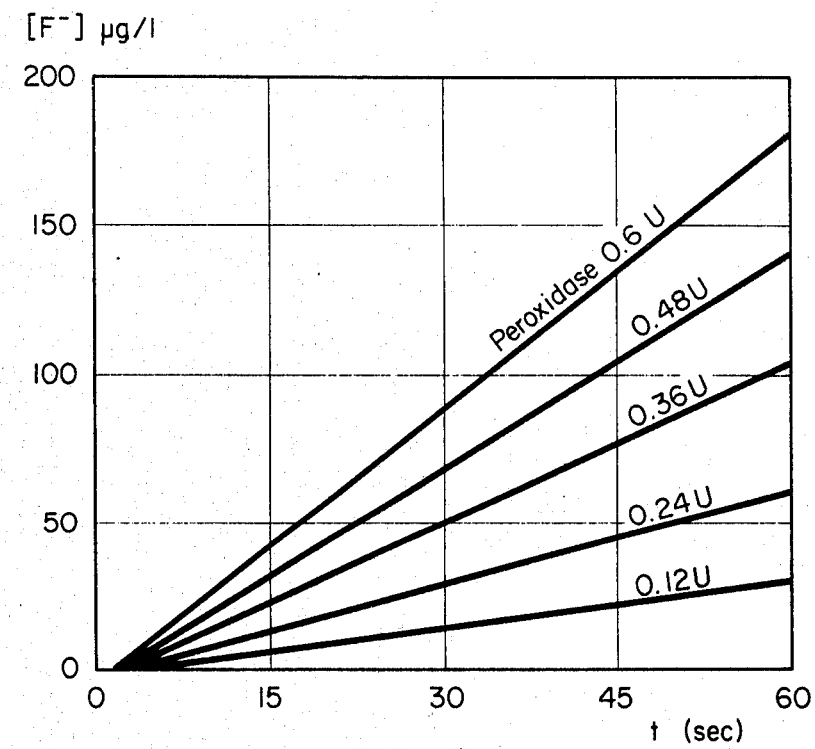
FIG. 5a is a graph showing the kinetics of F$^-$ formation in systems used for measuring variable amounts of peroxidase in the presence of an excess of H$_2$O$_2$.
Figure 5B:
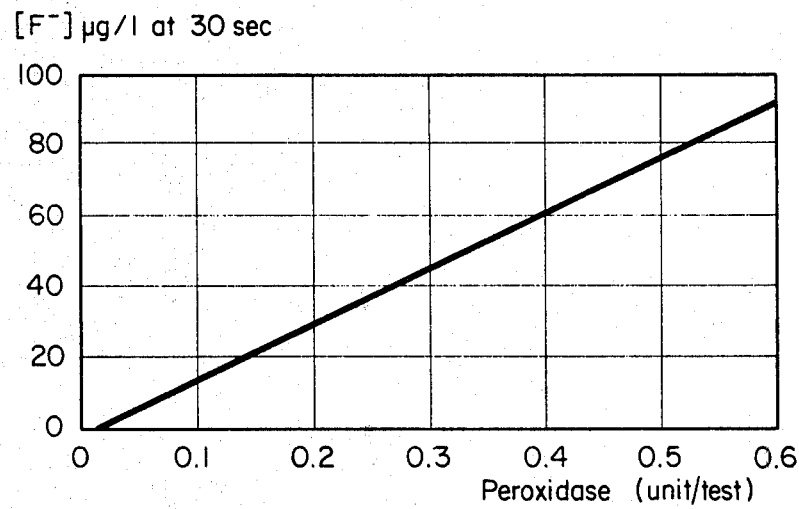
FIG. 5b is a plot of the slopes at 30 sec of the curves of FIG. 5a versus the corresponding peroxidase content of the samples.

Then, the analysis was carried out as in the previous Examples with 4.8 ml of $S_{CF}$ solution, 0.1 ml of the $H_2O_2$ solution and to this were added, under stirring, at 20° C. (±0.1° C.), 0.1 ml of one of the $S_E$ solutions. Zero time for the measurement was the moment of the addition of the peroxidase. Then, the kinetic developpement of F$^-$ was recorded and the values at t=30 sec were used as previously as the characteristic parameters. FIG. 5a shows the plot of time (sec) versus [F$^-$] (μmoles/l) calculated from the mV values as described previously. FIG. 5b shows the slope dV/d [F$^-$] plotted versus peroxidase concentration. The chart of FIG. 5b was thereafter used for measuring unknown amounts of peroxidase in immunology tests.

It is useful to note that in the present test, $S_{CF}$ solutions containing as low as 0.05 g/l of p-fluoroaniline worked as well as those containing 5 g/l.

It is also useful to remark that 0.1 ml (test quantity) of the $H_2O_2$ stock solution contains actually 5 μmoles of $H_2O_2$. Since, according to accepted standards, 1 unit of peroxidase consumes 1 μmole of $H_2O_2$/min, it is easily seen that in the case of the highest peroxidase concentration tested above (0.6 U of peroxidase involved) the amount of $H_2O_2$ consumed after 30 sec is about 1/20 of the available quantity. Therefore, the change in concentration can be considered negligible.

EXAMPLE 6

This Example refers to the measurement of glucose oxidase in a medium containing an excess of glucose.

(i) Solution of p-fluoroaniline and glucose $S_{CF}$: This solution was prepared as usual by dissolving 5 mg of p-fluoroaniline, 3 g of glucose and 1 ml of $10^{-3}$ M NaF solution in 0.3 M, pH 5.3, buffer (Tisals) and making up to 100 ml.

(ii) Peroxidase solution: This solution contained 60 U/ml.

(iii) GLucose oxidase standard solutions $S_E$: A set of 5 solutions was prepared which contained 0.1, 0.25, 0.5, 1 and 2 μ/ml, respectively.

Figure 6A:
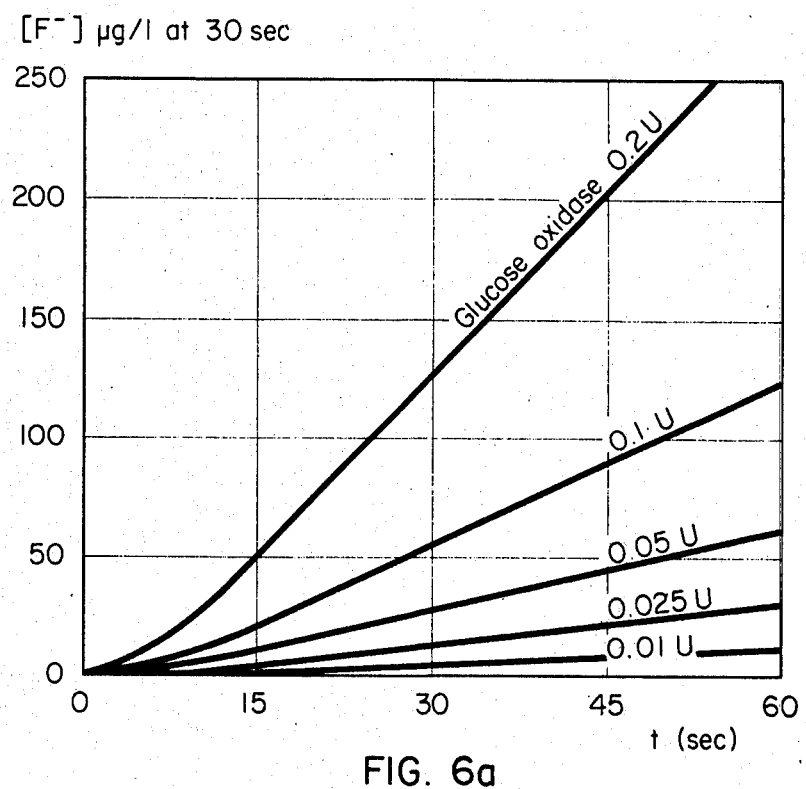
Figure 6B:
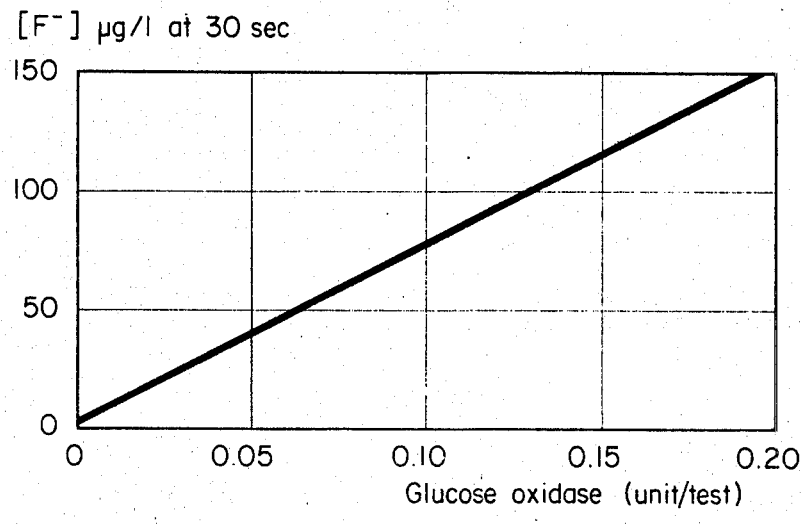
FIG. 6b is a plot of the slopes dV/dt at 30 sec of the curves of FIG. 6a versus glucose oxidase concentration.
Figure 7A:
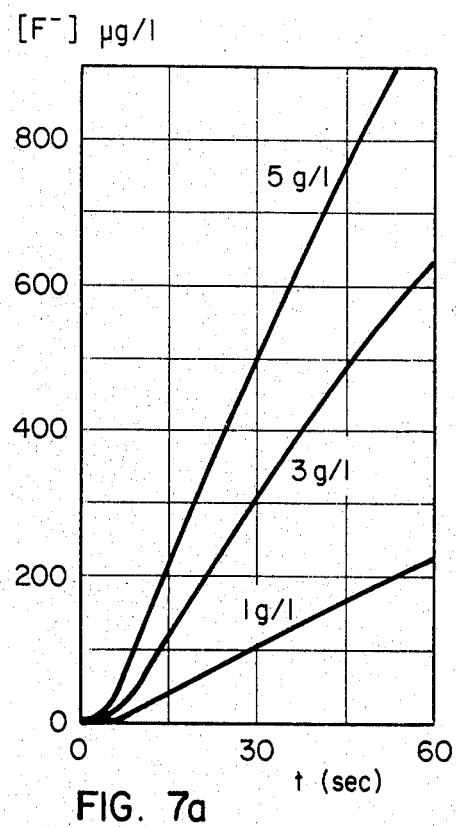
Figure 8A:
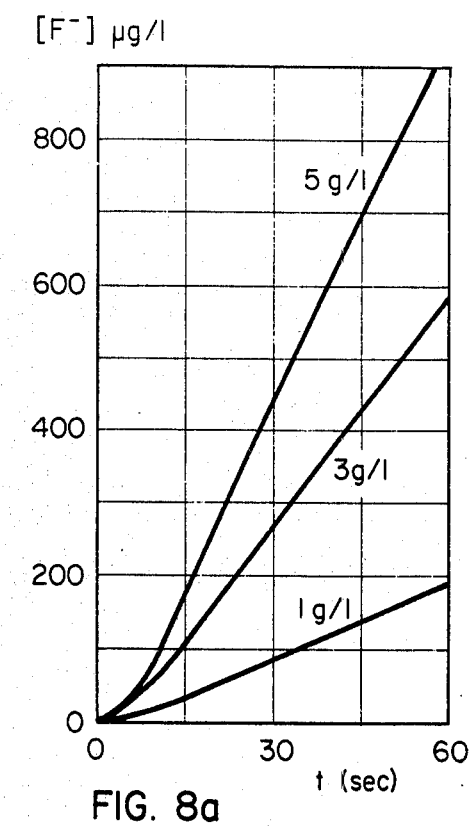
Figure 7B:
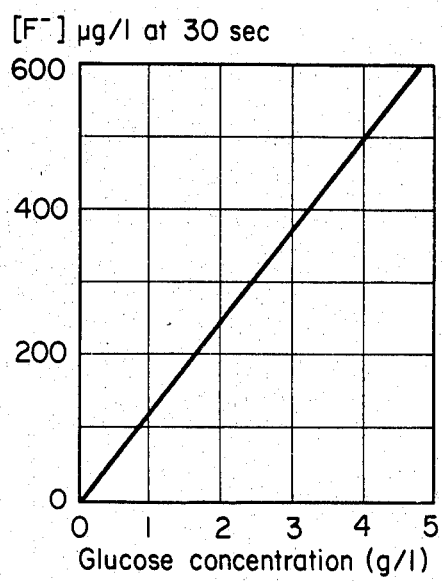
Figure 8B:
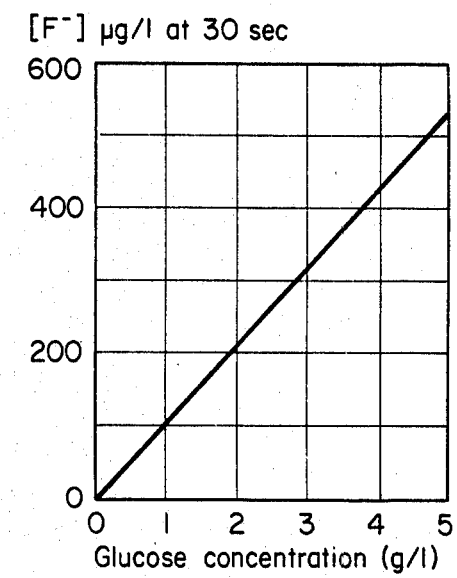
Figure 9A:
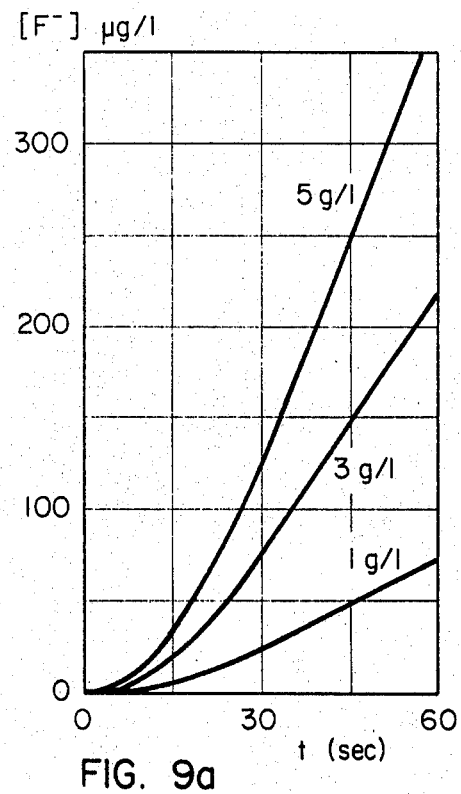
Figure 10A:
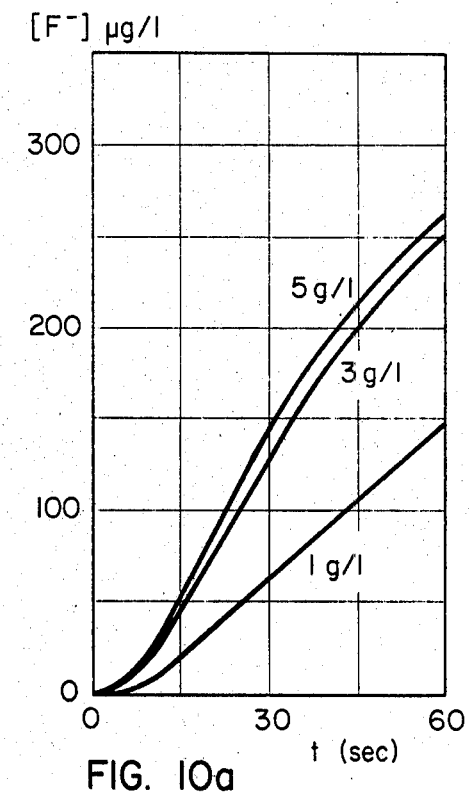
Figure 9B:
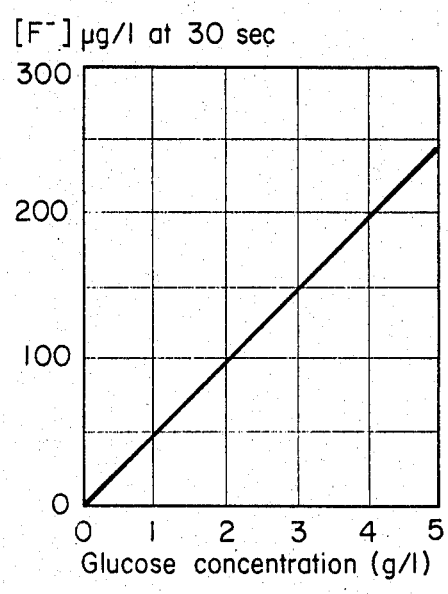
Figure 10B:
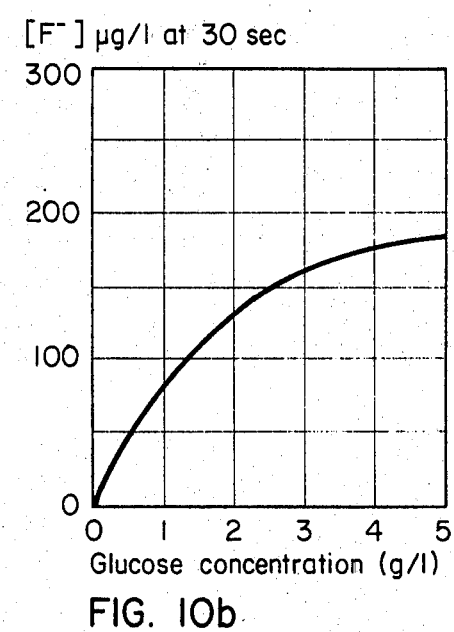

The analysis was conducted as before. 4.8 ml of $S_{CF}$ and 0.1 ml of the peroxidase solution (6 U) were agitated magnetically in a polyethylene beaker and, at $t_o$, 0.1 ml of the $S_E$ solution was added. The response of the F$^-$ sensitive electrode (which has been calibrated earlier with known NaF solution) was recorded for one minute and a graph of the rate curves (time versus [F$^-$]) was prepared. This is shown in FIG. 6a. Thereafter, the slope at 30 sec of each curve was plotted against glucose oxidase concentration to give the chart of FIG. 6b. This chart was then used successfully to compute the results from further measurements of the same kind with samples containing unknown amounts of glucose oxidase.

It should be kept in mind that the above Examples have not yet been optimized and that the above directions are possibly not the best way of carrying out the invention.

As stated hereinbefore, the invention can serve to achieve many analytical measurements of many substrates capable of being enzymatically (or otherwise catalytically) oxidized by oxygen (or air) with the quantitative production of hydrogen peroxide. The following Table summarizes some of the possibilities in this field and provides a list of enzymes, the substrates they may act upon as oxidation catalysts and the products resulting from said oxidation.

TABLE

| Enzyme | Substrate | Product |
|---|---|---|
| Glycollate oxidase | Glycollates | Glyoxylates + $H_2O_2$ |
| Pyruvate oxidase | Pyruvates + orthophosphates | Acetylphosphates + $CO_2$ + $H_2O_2$ |
| Oxalate oxidase | Oxalates | $CO_2$ + $H_2O_2$ |
| 2-Oxido reductase | L-gulono- -lactone | L-ascorbate + $H_2O_2$ |
| Alcohol-oxygen-oxido-reductase | Primary alkyl and aryl-alcohols | Aldehydes + $H_2O_2$ |
| L-gulonolactone oxidase | L-gulono- -lactone | L-xylohexulono-lactone + $H_2O_2$ |
| Galactose oxidase | D-galactose | D-galacto-hexodialdose + $H_2O_2$ |

TABLE-continued

| Enzyme | Substrate | Product |
| --- | --- | --- |
| Pyridoxin-4-oxidase | Pyridoxin | Pyridoxal + $H_2O_2$ |
| 2-Hydroxyacid oxidase | 2-hydroxyacids | 2-oxo-acids + $H_2O_2$ |
| D-aspartate oxidase | D-aspartate | Oxaloacetate + $H_2O_2$ |
| D and L-amino-acid oxidases | D and L-amino-acids | 2-oxo-acids + $H_2O_2$ |
| Pyridoxamine phosphate oxidase | Pyridoxamine phosphate | Pyridoxal phosphate + $H_2O_2$ + $NH_3$ |
| D-glutamate oxidase | D-glutamate | 2-oxoglutamate + $H_2O_2$ + $NH_3$ |
| Ethanolamine oxidase | Ethanolamine | Glycolaldehyde + $NH_3$ + $H_2O_2$ |
| Sarcosine oxidase | Sarcosine | Glycine + HCHO + $H_2O_2$ |
| N—methylaminoacid oxidase | N—methyl-L-amino-acids | L-amino-acids + HCHO + $H_2O_2$ |
| 6-hydroxy-L and D-nicotine oxidases | 6-hydroxy-L and D-nicotine | Ketones + $H_2O_2$ |
| Glyoxylate oxidase | Glyoxylate | Oxalate + $H_2O_2$ |
| Tyramine oxidase | Tyramine | 4-hydroxyphenyl-acetaldehyde + $H_2O_2$ |
| 3-Hydroxyanthranilate oxidase | 3-Hydroxyanthranilate | 1,2-benzoquinone-imine-3-carboxylate + $H_2O_2$ |

It should also be noted that other organic fluoro-compounds can be used in the present invention which may split their C-F bond with $H_2O_2$ in the presence of a peroxidase, the rate of this splitting being in proportion to the amount of $H_2O_2$. Also the selection of the other reagents involved in the present analysis: buffers, surfactants, preservative, etc. and the relative quantities of such ingredients can be varied according to the needs. Adaptations and modifications can thus be made to the present procedure by any skilled technician.

As a modification of the present rate reading technique, it is also possible to contemplate using, as a key parameter, the equilibrium potential reached for each sample after a given reaction time. This time shall be determined experimentally as the most suitable for reproducible results. This technique will therefore be based on a static type of determination related to the reaching of a fixed equilibrium of the enzymatic reaction, this being according to the well-known methods called "end point determination". For carrying out such modification, the equilibrium potential $V_e$ will be measured with each sample and the relationship between $V_e$ and the corresponding concentration of the samples will be established. Such modification is well suited for being adapted to automatic measurement systems. Thus, such a system would comprise a memory for storing the above-mentioned relationship data, an automatic circulating and mixing device for taking up the samples and contacting them with the reagents, an electrometric cell for measuring the potentials and a computing unit for comparing the measured values with the stored data, thus directly and automatically providing the desired results.

Moreover, the general procedure described in the present Examples, and particularly in regard to FIGS. 4a and 4b, could also be automated since calibrating rate data can also be processed electronically and stored in a memory (e.g. the dV/dt or d[$F^-$]/dt parameters), after which actual rate measurement for unknown sample could be computerized against said stored data in order to automatically furnish the desired analytical results.

Further Examples Nos. 7 to 17 illustrate the use of fluoro compounds other than p-fluoroaniline. The behavior of some of these compounds (7 to 10) in the analysis of glucose in the presence of glucose oxidase and peroxidase is also illustrated in correspondingly numbered FIGS. 7a to 10a and FIGS. 7b to 10b. The Figures with subscript a all concern rate curves obtained by measuring 0.1 ml samples containing 1 g/l, 3 g/l and 5 g/l of glucose, respectively, in the presence of 6 U of peroxidase, 30 U of glucose oxidase and 4.8 mg of the fluoro-compound, the analysis being carried out in a pH 5.3 acetate buffer in the presence of $10^{-5}$ M NaF, whereas the figures with subscript b concern the dV/dt data at 30 sec plotted against glucose concentration. Also, such fluoro-compounds are listed in the following table which indicates, all analytical conditions being the same, the relative behavior of such compounds compared to that of p-fluoroaniline. Therefore, the results recorded in the table show, among such compounds, which are suitable (+) for the measurements according to the invention, which are not (−) and which are questionable (+ −)

| Example | Compound | Suitability |
| --- | --- | --- |
| 7 | p-fluoroaniline | + |
| 7 | p-fluorophenol | + |
| 8 | 2,3,5,6-tetrafluorophenol | + |
| 9 | 5-fluoro-2-methylaniline | + |
| 10 | 4-fluoroanisole | + |
| 11 | 2,3,4,6-tetrafluoroaniline | + − |
| 12 | 1-(p-fluorophenyl)-piperazine | + − |
| 13 | p-fluorobenzyl alcohol | − |
| 14 | p-fluorobenzylamine | − |
| 15 | 4-fluorobiphenyl | − |
| 16 | hexafluorobenzene | − |
| 17 | 1,2,4,5-tetrafluorobenzene | − |

+ means that the CF bond was quantitatively cleaved during the test, whereas + − means that the reaction was not quantitative under the conditions used and − means that no liberation of fluoride was measured.

I claim:

1. A method of quantatively determining a constituent selected from the group which consists of hydrogen peroxide and peroxidase in an aqueous sample, said method comprising the steps of:

(a) mixing said sample with a reaction system selectively containing a known amount of peroxidase or hydrogen peroxide, respectively, and in excess of an organic fluorine compound in the form of a fluoroaniline, a fluoroanisole or a fluorophenol having at least one C—F bond cleaving on a peroxidase catalyzed oxidation by hydrogen peroxide whereby F⁻ ions are formed in the system;

(b) exposing the reaction system to an F⁻ selective electrode; and (c) electrochemically measuring by said electrode the rate of formation of F⁻ ions liberated by the peroxidase catalyzed cleavage of said C—F bond.

2. The method defined in claim 1 in which said sample is to be analyzed for hydrogen peroxide wherein said system is provided with a concentration of peroxidase sufficient to generate a rate of F⁻ formation for measurement over a limited period of time, and maintaining said concentration constant for a range of comparative analytical measurements.

3. The method defined in claim 2 wherein said reaction system is prepared by combining a buffer, said peroxidase and said fluorine compound and mixing said sample therewith, the rate of change of the potential of said electrode by measurement and the rate data thus obtained being compared with standardizing data with previous controlled analysis carried out identically on calibrating solutions of known hydrogen peroxide concentration.

4. The method defined in claim 1 wherein said sample contains peroxidase and said system is provided with sufficient hydrogen peroxide to maintain the concentration thereof substantially constant for the period in which the formation rate of F⁻ is measured.

5. The method defined in claim 1, 2, 3 or 4 wherein said organic fluorine compound is selected from the group which consists of p-fluoroaniline, p-fluorophenol, 2,3,5,6-tetrafluorophenol, 5-fluorophenol, 5-fluoro-2-methylaniline and p-fluoroanisole.

6. A method of quantitatively determining in an aqueous medium, an organic substrate sample, which comprises the steps of:

(a) preparing an aqueous reagent solution containing at least a buffer, a conjugate oxidase specific to said organic substrate and capable of oxidizing said organic substrate to yield $H_2O_2$ as an oxidation product, a peroxidase, and an organic fluoro compound selected from the group of a fluoroaniline, a fluorophenol, and a fluoroanisole, the C—F bond of which is cleavable with quantitative liberation of F⁻ ion by peroxidase-catalyzed oxidation with the $H_2O_2$ produced during the oxidase-catalyzed oxidation, the rate of the peroxidase-catalyzed oxidation being much greater than the rate of the oxidase-catalyzed oxidation, and the amount of the organic fluoro compound present being in excess of the rate limiting amount thereof for the peroxidase-catalyzed oxidation;

(b) mixing said aqueous reagent solution in excess of the rate limiting amount thereof for the oxidase-catalyzed oxidation with the organic substrate sample to be analyzed to oxidize the organic substrate to form hydrogen peroxide, said hydrogen peroxide then oxidizing the organic fluoro compound in the presence of the peroxidase to quantitatively split off F⁻ ion;

(c) measuring, in said mixture formed in step (b), with an F⁻ ion selective electrode the rate variation of the potential of said electrode with time during the peroxidase splitting reaction of said F⁻ ion;

(d) comparing said potential rate data thus obtained with standard rate potentials resulting from calibration analysis carried out previously on samples containing known concentrations of the same organic substrate being analyzed; and (e) correlating the value measured in step (c) with the standard data corresponding to the known concentration of said substrate expressed in step (d) so as to determine the concentration of the organic substrate to be analyzed.

7. The method defined in claim 6, step (a) wherein the concentration of the conjugate oxidase is sufficient to enable the rate of $H_2O_2$ formation to be measurable over a limited period of time and keeping said concentration constant from run to run for a full set of comparative analytical measurements.

8. The method defined in claim 6 wherein said organic substrate to be analyzed is glucose or cholesterol and wherein the conjugate oxidase is respectively glucose oxidase and cholesterol oxidase.

9. The method defined in claim 6, step (a), wherein the organic fluoro compound is selected from the group consisting of p-fluoroaniline, p-fluorophenol, 2,3,5,6-tetrafluorophenol, 5-fluorophenol, 5-fluoro-2-methylaniline and p-fluoro-anisole.

10. A method of quantitatively determining in an aqueous medium, a conjugate oxidase of an organic substrate, which comprises the steps of:

(a) preparing an aqueous reagent containing at least a buffer, a peroxidase, an organic substrate for which the conjugate oxidase is specific, said organic substrate being capable of oxidation by said conjugate oxidase to yield $H_2O_2$ and said organic substrate being present in excess of the rate limiting amount for the oxidase-catalyzed oxidation, and an organic fluoro compound selected from the group consisting of a fluoroaniline, a fluorophenol, and a fluoroanisole, the C—F bond of which is cleavable with quantitative liberation of F⁻ ion by peroxidase-catalyzed oxidation with the $H_2O_2$ produced during the oxidase-catlyzed oxidation, the rate of the peroxidase-catalyzed oxidation being much faster than the rate of the oxidase-catalyzed oxidation, and the amount of the organic fluoro compound present being in excess of the rate limiting amount for the peroxidase-catalyzed oxidation;

(b) immersing in said aqueous reagent solution an F⁻ selective electrode;

(c) mixing said aqueous reagent solution with a sample containing the conjugate oxidase to be analyzed in order to oxidize the organic substrate to form hydrogen peroxide, said hydrogen peroxide then oxidizing the organic fluoro compound in the presence of the peroxidase to quantitatively split off F⁻ ion, and measuring the variation of the potential of said F⁻ selective electrode with time in response to change in the [F⁻]; and (d) comparing said potential rate data thus obtained, or the corresponding [F⁻] data collected from the Nernst equation, with standard rate potentials, or corresponding standard [F⁻] data, resulting from calibration analysis carried out earlier on samples containing known concentrations of the conjugate oxidase to be analyzed, and correlating said values measured during step (c) with said standard data to obtain the desired results.

11. The method defined in claim 10, step (a), wherein the organic substrate is present in excess of the rate limiting amount for the oxidase-catalyzed oxidation to the extent that its concentration will remain approximately constant during the period when the rate of the hydrogen peroxide formation is measured.

12. The method defined in claim 10 wherein the conjugate oxidase to be analyzed is glucose oxidase or cholesterol oxidase and wherein the respective organic substrate is glucose or cholesterol.

13. The method defined in claim 10, step (a), wherein the organic fluoro compound is selected from the group consisting of p-fluoroaniline, p-fluorophenol, 2,3,5,6-tetrafluorophenol, 5-fluorophenol, 5-fluoro-2-methylaniline and p-fluoro-anisole.

* * * * *